US00PP08879P

United States Patent [19]

Danziger

[11] Patent Number: Plant 8,879

[45] Date of Patent: Sep. 6, 1994

[54] PETUNIA PLANT NAMED CAS 1

[75] Inventor: Gabriel Danziger, Post Beit Dagan, Israel

[73] Assignee: Florfis AG, Binningen, Switzerland

[21] Appl. No.: 162,351

[22] Filed: Dec. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of Petunia plant named Cas 1, characterized by the combined features of comparatively small dark purple-violet flowers, profuse flowering, medium to strong growth habit, overhanging plant habit, and dark green foliage.

2 Drawing Sheets

The present invention comprises a new and distinct cultivar of Petunia, hereinafter referred to by the cultivar name Cas 1.

Cas 1 was originated from a hybridization made by the inventor Gabriel Danziger in a controlled breeding program in Moshav Mishmar Hashiva, Israel in 1992. The female parent was a seedling designated X 57. The male parent of Cas 1 was a seedling designated Y 93. Both parents are proprietary cultivars used in the breeding program.

Cas 1 was discovered and selected as one flowering plant within the progeny of the stated cross by Gabriel Danziger in 1992 in a controlled environment in Moshav Mishmar Hashiva, Israel.

The first act of asexual reproduction of Cas 1 was accomplished when vegetative cuttings were taken from the initial selection in December 1992 in a controlled environment in Moshav Mishmar Hashiva, Israel, by, or under the supervision of, Gabriel Danziger.

Horticultural examination of selected units initiated in December 1992 and continuing thereafter has demonstrated that the combination of characteristics are herein disclosed for Cas 1 are firmly fixed and are retained through successive generations of asexual reproduction.

Cas 1 has not been observed under all possible environmental conditions. The phenotype may vary significantly with variations in environment such as temperature, light intensity and day length, without however, any variations in genotype.

The following observations, measurements, and comparisons describe plants grown in Hillscheid, Germany, under greenhouse conditions which approximate those generally used in commercial practice.

The following traits have been repeatedly observed and are determined to be basic characteristics of Cas 1, which in combination distinguish this Petunia as a new and distinct cultivar:

1. Comparatively small, dark purple-violet flowers.
2. Profuse flowering.
3. Medium to strong growth habit, with branches fully extending in all directions from center of plant.
4. Overhanging plant habit.
5. Dark green foliage.

Of the commercial cultivars known to the present inventor, the most similar in comparison to Cas 1 is Revolution. Cas 1 has a darker, more bluish shade of flower color, and the plant size of Cas 1 (100 cm) is not as long as Revolution (130 cm). Other characteristics are similar as that of Revolution.

The accompanying photographic drawings show typical flower and foliage characteristics of Cas 1, with colors being as true as possible with illustrations of this type.

The photograph on Sheet 1 illustrates Cas 1 cultivated in a hanging basket.

The photo on Sheet 2 comprises an enlarged showing of single flowers of the new cultivar.

In the following description, color references are made to The Royal Horticultural Society Color Chart. The color values were determined indoors in August. Flowers were taken from plants cultivated in hanging baskets in an open greenhouse in Hillscheid, Germany, For the description, the upper parts of the plants were observed or measured.

Classification:

*Botanical.*—A hybrid of the genus Petunia.

*Commercial.*—Petunia cv Cas 1.

INFLORESCENCE

Plant:

*Growth habit.*—Vigorous, drooping.

*Plant length.*—100 cm (28 week old plants).

*Blooming period.*—Early; begins 9 weeks after propagation of unrooted cuttings, continually flowering thereafter.

Stem:

*Thickness.*—Young branches: 2–3 mm; Older branches 4–5 mm.

*Color.*—Medium green, 137 C.

*Pubescence.*—Present.

*Branching.*—10–12 branches per week.

*Length of internode.*—15–25 mm.

Leaf:

*Arrangement on stem.*—Opposite, arranged decussately on stem.

*Shape.*—Ovate or narrow-ovate.

*Size (average).*—45 mm long, 26 mm broad, based on largest leaves from a young stem of a plant in flower.

*Thickness.*—Thin.

*Color.*—Dark green, 137A.

*Pubescence.*—Present but weak.

Flower:

*Orientation at opening.*—The bud and peduncle form an acute angle with the stem; the open flower and peduncle are oriented approximaqtely at right angles to the stem.

*Type.*—Single.

*Shape.*—Not completely round, only weak lobes.

*Diameter* 50–55 mm (comparatively small).

*Color.*—Upper (inner) surface at opening: Between 83 A and 79 A. Under (outer) surface at opening: 83 B. Upper (inner) surface at pollen maturity: 83 A-B. Under (outer) surface at pollen maturity: 83 C. Throat (inner surface): Light violet, with dark net-shaped veining.

*Peduncle length.*—20–25 mm.

*Peduncle color.*—Medium green, with a small amount of anthocyanin near the base of the flower.

*Reproductive organs.*—Pistil: 1 green. Stammer: 5, fertile. Anther: Bluish white. Filament: White to light violet.

Resistance: Very good resistance to rain and good heat tolerance.

It is claimed:

1. A new and distinct cultivar of Petunia plant named Cas 1, as illustrated and described.

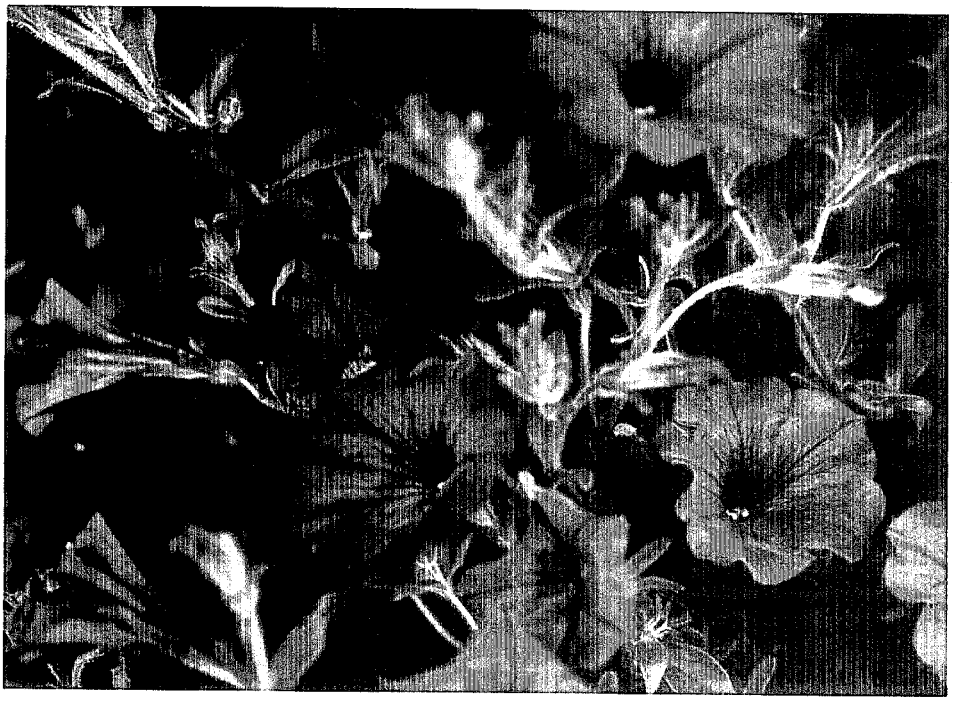

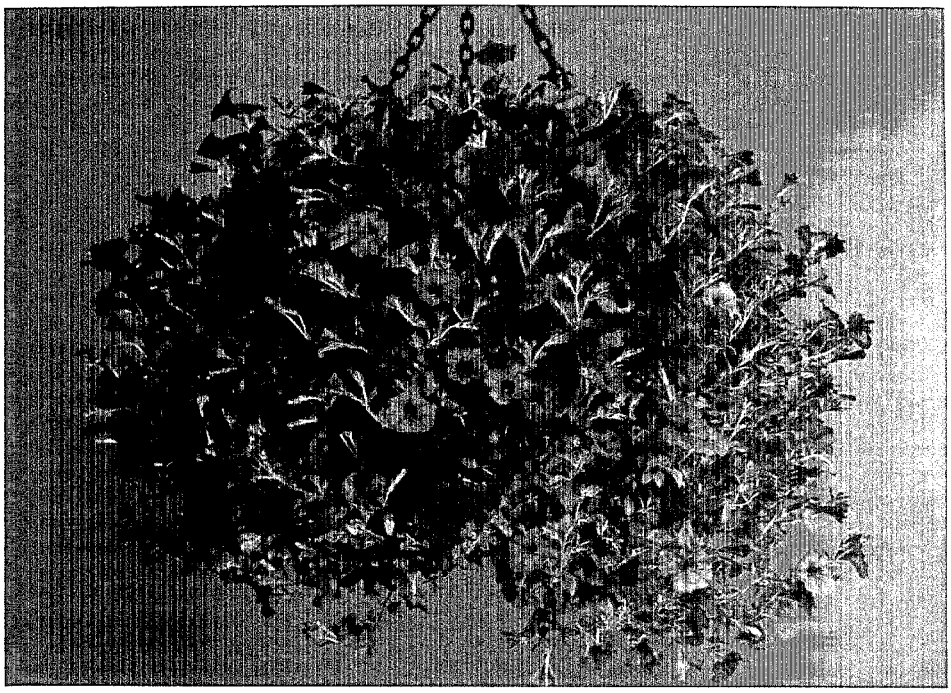

* * * * *